(12) United States Patent
Tan (10) Patent No.: US 11,707,317 B2
(45) Date of Patent: Jul. 25, 2023

(54) CONTACTLESS CIRCUITRY FOR CORDED SURGICAL DEVICES

(71) Applicant: COVIDIEN LP, Mansfield, MA (US)

(72) Inventor: Wei Tan, Shanghai (CN)

(73) Assignee: Covidien LP, Mansfield, MA (US)

( * ) Notice: Subject to any disclaimer, the term of this patent is extended or adjusted under 35 U.S.C. 154(b) by 965 days.

(21) Appl. No.: 16/476,472

(22) PCT Filed: Feb. 13, 2017

(86) PCT No.: PCT/CN2017/073353
§ 371 (c)(1),
(2) Date: Jul. 8, 2019

(87) PCT Pub. No.: WO2018/145310
PCT Pub. Date: Aug. 16, 2018

(65) Prior Publication Data
US 2020/0054389 A1    Feb. 20, 2020

(51) Int. Cl.
*A61B 18/14* (2006.01)
*A61B 17/32* (2006.01)
*A61B 18/16* (2006.01)
*A61B 17/00* (2006.01)
*A61B 17/29* (2006.01)
(Continued)

(52) U.S. Cl.
CPC .. *A61B 18/1445* (2013.01); *A61B 17/320092* (2013.01); *A61B 18/16* (2013.01);
(Continued)

(58) Field of Classification Search
CPC .. A61B 17/320092; A61B 2017/00039; A61B 2017/00221; A61B 2017/2929; A61B 2018/00178; A61B 2018/00589; A61B 2018/00595; A61B 2018/00827; A61B 2018/00916; A61B 2018/00928; A61B 2018/00988; A61B 2018/00994
See application file for complete search history.

(56) References Cited

U.S. PATENT DOCUMENTS 7,335,997 B2    2/2008    Wiener
8,992,555 B2    3/2015    Smith et al.
(Continued)

FOREIGN PATENT DOCUMENTS

CN    104519820 A    4/2015

OTHER PUBLICATIONS

Extended European Search Report issued in corresponding Appl. No. EP 17895880.7 dated Aug. 20, 2020 (6 pages).
(Continued)

*Primary Examiner* — Khadijeh A Vahdat
*Assistant Examiner* — Sean W Collins
(74) *Attorney, Agent, or Firm* — Carter, DeLuca & Farrell LLP (57) ABSTRACT

A surgical device (10) includes a handle (122) and a rotatable assembly (130) coupled and rotatable with respect to the handle (122). The surgical device (10) further includes a switch (126) coupled to the handle (122) and having a plurality of positions. A first inductor (1122) is coupled to the switch (126) and a second inductor (1102) is coupled to the rotatable assembly (130). A current signal propagating through the first inductor (1122) and/or a current signal propagating through the second inductor (1102) changes based on a position of the switch (126).

19 Claims, 5 Drawing Sheets

(51) Int. Cl.
*A61B 18/00* (2006.01)
*A61B 18/12* (2006.01)

(52) U.S. Cl.
CPC ............... *A61B 2017/00039* (2013.01); *A61B 2017/00221* (2013.01); *A61B 2017/2929* (2013.01); *A61B 2017/320074* (2017.08); *A61B 2018/00178* (2013.01); *A61B 2018/00589* (2013.01); *A61B 2018/00595* (2013.01); *A61B 2018/00666* (2013.01); *A61B 2018/00827* (2013.01); *A61B 2018/00916* (2013.01); *A61B 2018/00928* (2013.01); *A61B 2018/00988* (2013.01); *A61B 2018/00994* (2013.01); *A61B 2018/1286* (2013.01)

(56) References Cited

U.S. PATENT DOCUMENTS

| | | |
|---|---|---|
| 2001/0048356 A1 | 12/2001 | Owen |
| 2007/0157404 A1 | 7/2007 | Brewer et al. |
| 2010/0094288 A1 | 4/2010 | Kerr |
| 2011/0172660 A1 | 7/2011 | Bales, Jr. et al. |
| 2011/0213354 A1* | 9/2011 | Smith ................ A61B 18/1206 323/282 |
| 2012/0275098 A1 | 11/2012 | Feine |
| 2013/0274729 A1 | 10/2013 | Orszulak |
| 2013/0289591 A1* | 10/2013 | Boudreaux ........ A61B 18/1206 606/169 |
| 2014/0074085 A1* | 3/2014 | Kerr ................... A61B 18/1402 606/34 |
| 2014/0350545 A1 | 11/2014 | Moua et al. |

OTHER PUBLICATIONS

International Search Report and Written Opinion issued in corresponding Appl No. PCT/CN2017/073353 dated Nov. 2, 2017 (12 pages).

* cited by examiner

CONTACTLESS CIRCUITRY FOR CORDED SURGICAL DEVICES

TECHNICAL FIELD

The present disclosure generally relates to surgical systems, and, more particularly, to contactless circuitry for corded surgical devices.

BACKGROUND

Surgical systems and surgical devices using electrical energy in removal of tissue and cauterization of vessels have grown in popularity due in part to their effectiveness. For example, one typical such system is an ultrasonic scalpel that generates longitudinal vibrations with an ultrasonic transducer along an axis of a cutting blade. By placing a resonant wave along the length of the blade, high-speed longitudinal mechanical movement is produced at the end of the blade. Such instruments have grown in popularity in part because the mechanical vibrations transmitted to the end of the blade are very effective at cutting organic tissue and, simultaneously, coagulating the tissue using the heat energy produced by the ultrasonic frequencies. Therefore, such instruments are particularly well suited for use in minimally invasive procedures, such as endoscopic or laparoscopic procedures, where the blade is passed through a trocar to reach the surgical site.

Existing surgical systems and surgical devices typically fall into two categories—devices without a cord (cordless devices) and devices with a cord (corded devices). Cordless devices, while untethered from additional components such as an external generator, are typically heavier than corded devices and thus put a greater burden on the hands of the surgeon. Corded devices on the other hand are lighter for surgeons to maneuver and are thus sometimes preferred by surgeons. However, with corded surgical devices technical challenges arise in allowing for independent motion between a rotatable portion and a stationary portion of the device while maintaining power and/or signal communication across the boundary between the rotatable portion and the stationary portion of the device, for example between an external generator and the stationary portion of the surgical device handpiece. Prior approaches utilize metal contact rings or spring beads to maintain electrical contact throughout rotation. However, such components can be cost ineffective for disposable surgical devices, and can increase the difficulty of fabrication and assembly of surgical devices. Given the foregoing, there is a need for improved systems and methods for facilitating independent motion between a rotatable portion and a stationary portion of a corded surgical device.

SUMMARY

According to an aspect of the present disclosure, methods and systems are provided that address the above mentioned needs. In an aspect of the present disclosure, a surgical device is provided that includes a handle, a rotatable assembly, a switch, a first inductor, and a second inductor. The rotatable assembly is coupled to the handle and is rotatable with respect to the handle. The switch is also coupled to the handle and has a plurality of positions. The first inductor is coupled to the switch and the second inductor is coupled to the rotatable assembly. At least one of the first inductor, the second inductor, and/or the switch is configured such that at least one of a current signal propagating through the first inductor and/or a current signal propagating through the second inductor changes based on a position of the switch.

In another aspect of the present disclosure, the surgical device includes a coupling transformer formed by the first and second inductors.

In still another aspect of the present disclosure, at least one of the first inductor, and/or the second inductor is a contactless ring.

In yet another aspect, the first inductor and the second inductor are communicatively coupled to one another, and the first inductor and the second inductor are configured so as to remain communicatively coupled to one another at all positions of the rotatable assembly with respect to the handle.

In another aspect of the present disclosure, the handle is stationary with respect to the rotatable assembly.

In still another aspect of the present disclosure, the rotatable assembly includes an end effector.

In yet another aspect of the present disclosure, the surgical device is an ultrasonic surgical device.

In another aspect of the present disclosure, the surgical device is an energy-based (for example, a radio frequency energy-based) surgical device.

In accordance with another aspect of the present disclosure, a surgical system is provided that includes a surgical device, a generator, and a flexible electrical power cord. The surgical device includes a handle, a rotatable assembly, a switch, a first inductor, and a second inductor. The rotatable assembly is coupled to the handle and is rotatable with respect to the handle. The switch is also coupled to the handle and has a plurality of positions. The first inductor is coupled to the switch and the second inductor is coupled to the rotatable assembly. At least one of the first inductor, the second inductor, and/or the switch is configured such that at least one of a current signal propagating through the first inductor and/or a current signal propagating through the second inductor changes based on a position of the switch. The rotatable assembly is configured to be coupled to the generator by way of the flexible electrical power cord.

In another aspect, the surgical device includes a coupling transformer formed by the first and second inductors.

In still another aspect of the present disclosure, the first inductor and the second inductor are communicatively coupled to one another, and the first inductor and the second inductor are configured so as to remain communicatively coupled to one another at all positions of the rotatable assembly with respect to the handle.

In another aspect of the present disclosure, the generator includes an electrical current sensor.

In yet another aspect of the present disclosure, the electrical current sensor is configured to be coupled to the second inductor by way of the flexible electrical power cord and detect the current signal propagating through the second inductor.

In another aspect of the present disclosure, the generator is configured to deliver a driving signal to the rotatable assembly, via the flexible electrical power cord, in response to the electrical current sensor detecting a threshold amount of current across the second inductor.

In still another aspect of the present disclosure, the surgical device includes a plurality of switches each capable of being set to at least one of a plurality of positions. The first inductor is coupled to the plurality of switches by way of a plurality of circuit paths, respectively. At least one of the first inductor, the second inductor, and/or the plurality of switches is configured such that at least one of the current signal propagating through the first inductor and/or the current signal propagating through the second inductor changes based on at least one of the plurality of positions to which at least one of the plurality of switches is set. The electrical current sensor detects an attribute of a current signal propagating through the second inductor based on the at least one of the plurality of positions to which at least one of the plurality of switches is set. The generator delivers a driving signal to the rotatable assembly, via the flexible electrical power cord, based on the attribute of the current signal propagating through the second inductor and detected by the electrical current sensor.

In yet another aspect of the present disclosure, the generator further includes a processor as well as a memory unit coupled to the processor. The memory unit stores sequences of instructions which, when executed by the processor, cause the processor to deliver a driving signal to the rotatable assembly.

In still another aspect of the present disclosure, the memory further stores sequences of instructions which, when executed, cause the processor to receive information relating to an operating mode of the surgical device and deliver, based on the information relating to the operating mode of the surgical device, a particular driving signal to the rotatable assembly.

In another aspect of the present disclosure, the operating mode of the surgical device is a radio frequency mode and the particular driving signal delivered to the rotatable assembly is a radio frequency signal.

In yet another aspect of the present disclosure, the operating mode of the surgical device is a cauterization mode and the memory further stores sequences of instructions which, when executed, cause the processor to deliver, as the driving signal, a signal corresponding to the cauterization mode. In another aspect of the present disclosure, the operating mode of the surgical device is a coagulation mode and the memory further stores sequences of instructions which, when executed, cause the processor to deliver, as the driving signal, a signal corresponding to the coagulation mode.

BRIEF DESCRIPTION OF THE DRAWINGS

Various aspects and features of the present disclosure are described hereinbelow with references to the drawings, wherein.

DETAILED DESCRIPTION

The present disclosure is directed to contactless circuitry for corded surgical devices. Embodiments of the present disclosure are now described in detail with reference to the drawings in which like reference numerals designate identical or corresponding elements in each of the several views. As used herein, the term "clinician" refers to a doctor, a nurse, support personnel or any other person that may use integrated training system described herein to train on bronchoscopy techniques. Throughout this description, the term "proximal" will refer to the portion of the device or component thereof that is closer to the clinician and the term "distal" will refer to the portion of the device or component thereof that is farther from the clinician. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

As described above, the existing surgical systems and surgical devices are typically either devices that implement (1) a cordless design, or a (2) corded design. Surgical devices implementing a cordless design are powered by a battery that is implemented within the device. These devices also include a generator that transmits a driving or electrical signal to a transducer on the device. These design choices help avoid the inconvenience experienced by a clinician during the movement of a device that implements a corded design. However, devices implementing a cordless design are heavier than devices that implement a corded design because of the additional weight of the battery and the generator that are implemented within the device. Furthermore, the additional weight resulting from the cordless design is added to the handle portion or handpiece of the surgical device, burdening a clinician who operates the device.

While devices implementing a corded design are lighter than devices implementing a cordless design, such devices typically require implementing contact rings in the device in order to maintain electrical connection between the handle portion or a stationary portion of the device and a rotatable portion of the device. However, manufacturing devices with the contact rings increases manufacturing complexity and cost, which makes the corded device less favorable, especially in emerging markets. The present disclosure generally provides for a surgical device that utilizes contactless rings to maintain an electrical connection between the handle portion or stationary portion of the device and the rotatable portion of the device, for example to facilitate maintained power and/or signal communication across the boundary between the rotatable portion and the stationary portion of the device.

Figure 1:
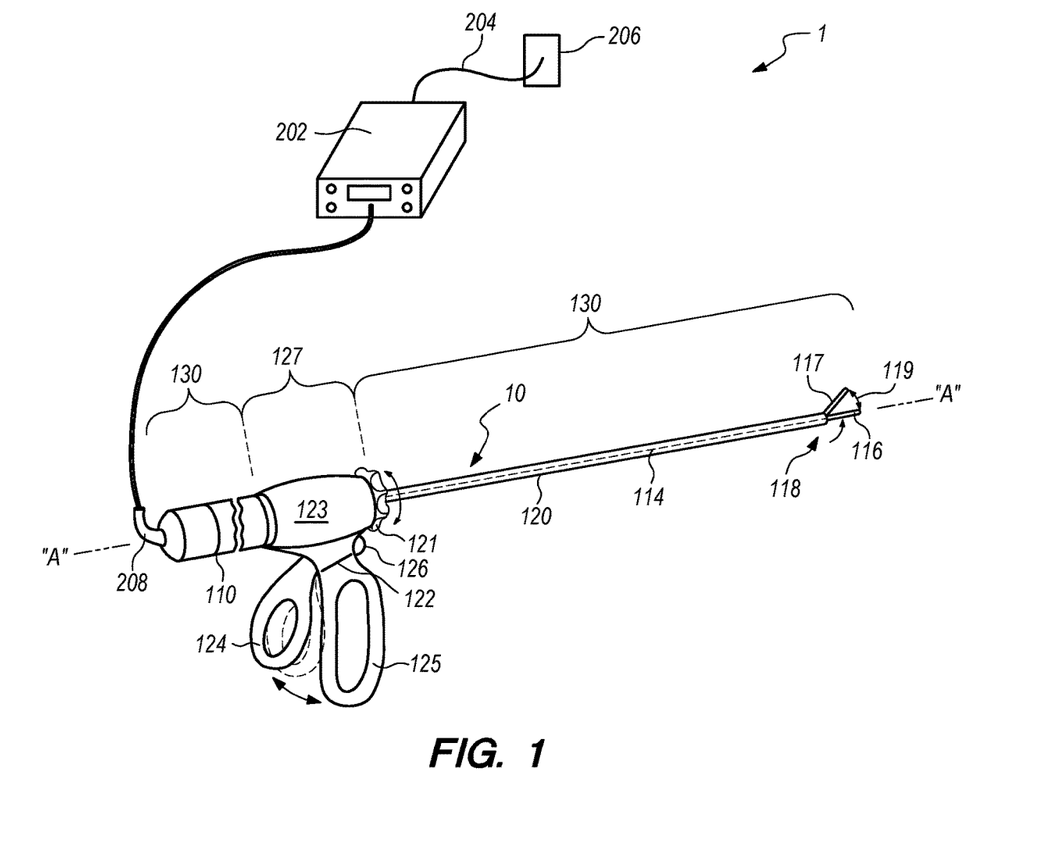
FIG. 1 is a perspective view, which shows one illustrative embodiment of an integrated corded surgical system, in accordance with the present disclosure.

Referring to FIG. 1, an integrated corded surgical system 1 is shown, which includes a surgical device 10 and a generator 202. The present disclosure is provided in the context of a surgical device 10 that is an ultrasonic scalpel. However, an ultrasonic scalpel is merely one example surgical device and the present disclosure is similarly applicable to other types of surgical devices 10, such as radio frequency or microwave energy-based surgical devices, and/or the like. As one of skill in the art would appreciate, in embodiments where the surgical device 10 is not an ultrasonic scalpel but rather is another type of surgical device, various aspects of the surgical device 10 (for instance, the housing unit 123, the handle assembly 122, the end effector assembly 118, the jaw members 116, 117, the switch 126, and/or the like) may be vary from the particular configuration of the ultrasonic scalpel surgical device 10 illustrated in FIG. 1. The surgical device 10 includes a housing unit 123, a handle assembly 122, and a rotatable assembly 130. The rotatable assembly 130 includes a transducer 110, a rotatable wheel 121, a shaft 120, and an end effector assembly 118. The end effector assembly 118 is located at a distal portion of the surgical device 10 and coupled to the shaft 120. The end effector assembly 118, which includes jaw members 116, 117, is operatively coupled to the handle assembly 122 and the generator 202 via the shaft 120, the transducer 110 and a flexible power and/or data cord 208. The shaft 120 is operatively coupled to the rotatable wheel 121 and the transducer 110.

The rotatable wheel 121 is coupled to the transducer 110, which is operatively coupled to the generator 202 via the flexible cord 208. The transducer 110 is housed within the housing unit 123, which is coupled to the handle assembly 122. In some embodiments, the housing unit 123 includes the handle assembly 122. The rotatable wheel 121 is included within the housing unit 123 or, in some examples, is positioned flush with the housing unit 123 such that a portion of the rotatable wheel 121, such as a side of rotatable wheel 121, protrudes out of the housing unit 123. In some aspects, a portion of rotatable wheel 121 housed within the housing unit 123 protrudes laterally from the housing unit 123.

The end effector assembly 118 is configured as a unilateral assembly with a jaw member 116, configured to be fixed to the transducer 110, and a jaw member 117, configured to be pivotable relative to the jaw member 116 and the shaft 120 throughout a space 119. In other embodiments, the jaw member 117 is configured to be in a fixed position relative to the shaft 120 and the jaw member 116 is configured to be pivotable relative to the jaw member 117 and the shaft 120 throughout the space 119. In some embodiments, the end effector assembly 118 is configured as a bilateral assembly with the jaw members 116, 117 being pivotable relative to each other and the shaft 120 throughout the space 119.

In some embodiments, the surgical device 10 may be configured as a bipolar instrument, where at least one side of the jaw members 116, 117 includes a seal plate (not separately shown in FIG. 1). In such embodiments, for example, the seal plates of the jaw members 116, 117 are each configured as an electrode, where one of the seal plates is an active electrode and another one is a return electrode. Each seal plate is operatively coupled to one or more electrical leads (not shown in FIG. 1), at least a portion of which are housed within the shaft 120. The one or more electrical leads are operatively coupled to the generator 202 via the flexible electrical cord 208. Thus, each seal plate is electrically and operatively coupled to the generator 202 by way of the electrical leads, which extend through the shaft 120 and are at least partially housed within the shaft 120, and the flexible electrical cord 208.

In other embodiments, the surgical device 10 is configured as a monopolar instrument. In such embodiments, for example, the seal plate of one of the jaw members 116, 117 is configured as an active electrode, and a return electrode is established using a return electrode pad. The return electrode pad is placed under the patient such that electrical current flows from the generator 202 to the active electrode in the jaw members 116 or 117 through tissue of the patient to the return electrode pad and back to the generator 202.

The handle assembly 122 includes a movable portion 124 and fixed portion 125. In some embodiments, the handle assembly 122 is configured such that moving the movable portion 124 towards the fixed portion 125 moves the jaw members 116, 117 of the end effector assembly 118. The jaw members 116, 117 are configured to move throughout the space 119 in response to moving the movable portion 124 towards the fixed portion 125.

The rotatable wheel 121 is configured to be rotatable in either direction about the longitudinal axis "A-A." The shaft 120 is operatively coupled to the rotatable wheel 121 such that rotating the rotatable wheel 121 rotates shaft 120 about the longitudinal axis "A-A." Rotating the shaft 120 also rotates the end effector assembly 118. Thus rotating the rotatable wheel 121 rotates the end effector assembly 118.

In various embodiments, the handle assembly 122 includes a multiple-position switch 126. Each of the positions of the switch 126, in some examples, is configured to activate a particular operative mode. An operative mode, as described herein, is a particular operation that the surgical system 1 is configured to perform. Example operative modes that the surgical system 1 may be configured to perform include, but are not limited to, the generator 202 delivering, by way of the surgical device 10, radio frequency energy, microwave energy, ultrasonic energy, and/or another suitable type of energy. In some instances, the operative modes may also include surgical techniques used by clinicians in practice such as cauterization or cutting of tissue, coagulation of tissue, and/or the like. Similarly, one of the operative modes may, in some cases, be a low-power mode of operation and another one of the operative modes may be a high-power mode of operation.

For example, cauterization or cutting of tissue is initiated when the cauterization operative mode is selected. In response to the selection of the cauterization operative mode, a particular driving signal is delivered to the surgical device 10 from the generator 202. The particular driving signal includes a certain amount of current to be delivered to the surgical device 10 from the generator 202. The certain amount of current delivered from the generator 202 to surgical device 10 corresponds to the operative mode selected by the clinician. Continuing with the above example, when the cauterization mode is selected the amount of current delivered by generator 202 to the surgical device 10 is configured to be an amount of current that causes the tissue temperature to reach a threshold level sufficient to cut the tissue.

In some embodiments, one of the switches has at least two positions, with one of the positions being an "on" position and the other position being an "off" position, such that when the switch is in the "on" position, the surgical device 10 is operatively powered on (for example, causing ultrasonic oscillation of the jaw members 116, 117, delivering radio frequency energy, or the like) and when the switch is in the "off" position, the surgical device 10 is operatively powered off (for example, with no ultrasonic oscillation of the jaw members 116, 117, delivery of radio frequency energy, or the like). Such a switch is referred to herein as an "on-off" switch. In some embodiments, the handle assembly 122 also includes an indicator (not shown in FIG. 1) that corresponds to the position of the on-off switch. The indicator is configured to provide an alert to the clinician when the position of the switch is in the "on" position and provide a different alert or no alert to the clinician when the switch position is in the "off" position. The indicator may, for example, be a light emitting diode (LED) that is configured to be powered on or emit light when the on-off switch is turned "on" or in the "on" position and not emit light or powered off when the on-off switch is turned "off" or in the "off" position.

The transducer 110 coupled to the flexible cord 208 is configured to convert electrical energy or current delivered by the generator 202 via the flexible cord 208 into mechanical energy that is conveyed via a waveguide 114 to the distal portion of the surgical device 10. In particular, the waveguide 114 guides mechanical energy from the transducer 110 to produce a motion at the distal portion of the surgical device 10, such as at jaw members 116, 117. The transducer 110 is driven at a resonant frequency by the generator 202 such that ultrasonic motion is produced at the active jaw member, which is the one of the jaw members 116, 117 that is coupled to the active electrode. The ultrasonic motion produced at the active jaw member is used to treat tissue grasped or clamped between the jaw members 116, 117.

The generator 202 is coupled to a flexible power cord 204 that is configured to be plugged into an electrical outlet 206 to operatively couple the generator 202 to an electrical power source (not explicitly shown in FIG. 1) for supply of power. In various embodiments, the generator 202 may be a microwave generator or may be configured to deliver radio frequency energy or another type of energy. As described in further detail below in connection with FIG. 6, the generator 202 includes one or more processors coupled to one or more memory units storing one or more sequences of instructions that, when executed by the processor(s), cause the generator 202 to perform one or more functions. Additional details of the generator 202 and the surgical device 10 are also provided below in connection with FIGS. 2, 3, and 4.

Figure 2:
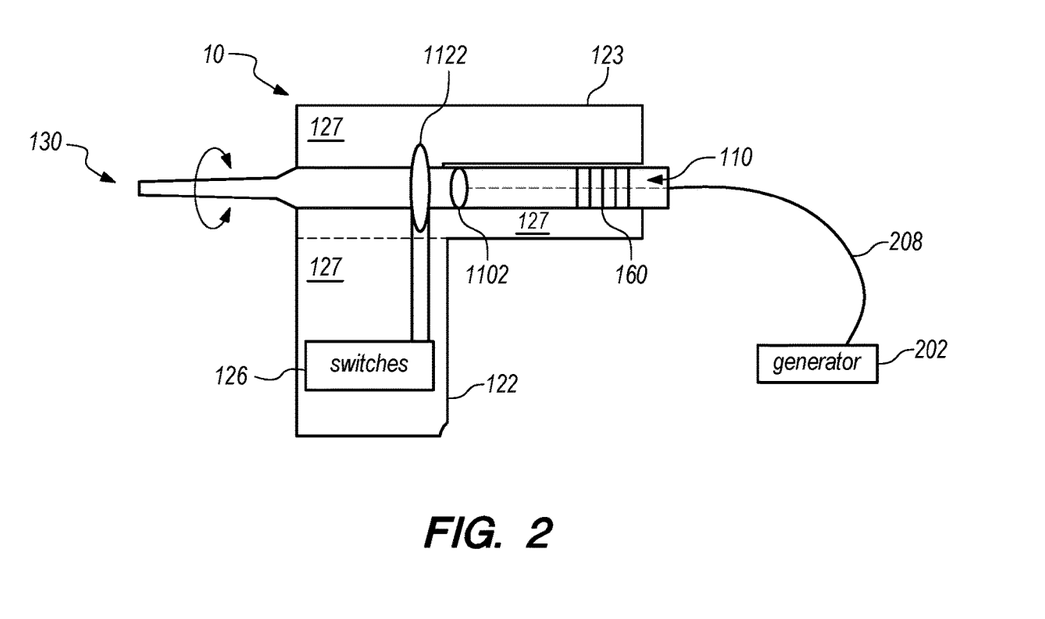
FIG. 2 is a schematic drawing showing additional details of the integrated corded surgical system of FIG. 1.

Referring now to FIG. 2, the transducer 110 includes one or more piezoelectric discs 160, which are operatively coupled to the generator 202 by way of one or more electrical conductors (not shown in FIG. 2) that are coupled to the piezoelectric discs 160 and are at least partially housed within the flexible cord 208. The stationary assembly 127, which includes the handle assembly 122 and the housing unit 123, is stationary relative to the rotatable assembly 130. The handle assembly 122 includes a switch 126, which is capable of being set to any one of multiple possible positions and is operatively coupled to an inductor 1122. In one example embodiment, the inductor 1122 is a contactless ring or coil, but the inductor 1122 may be any suitable type of inductor. The switch 126 is coupled to, or included as an integral part of, the stationary assembly 127, and, in some embodiments, is included within the handle assembly 122. The inductor 1122 is a contactless ring and is configured such that no portion of the inductor 1122 is part of the rotatable assembly 130. For example, the inductor 1122 may be housed within the stationary assembly 127, or may be housed entirely within the handle assembly 122. In some embodiments, portions of the inductor 1122 may be housed within the housing unit 123 and the handle assembly 122, however no portion of the inductor 1122 is housed or included within any portion of the rotatable assembly 130. As shown in FIG. 2, the inductor 1122 is coupled to the switch 126 by way of one or more circuit paths.

An inductor 1102 is included within the rotatable assembly 130. In one example embodiment, the inductor 1102 is a contactless ring or coil, and is electrically coupled to the generator 202 by way of the cord 208. However, the inductor 1102 may be any suitable type of inductor. The inductor 1102 is inductively coupled with the inductor 1122 and forms a weakly coupled transformer. The inductor 1122 is fixed on the handle assembly 122. When the inductor 1102 rotates with the rotatable assembly 130, the inductor 1122 housed within the housing 123 is stationary with respect to the handle assembly 122 and maintains the inductive coupling with the inductor 1102. In some embodiments, one or more electronic components are also housed within the rotatable assembly 130 or the generator 202. The one or more electrical conductors and/or components may, in some instances, be coupled to a power source unit, for example a power source unit 102 of the generator 202 (not shown in FIG. 2, but described in further detail below in connection with FIG. 5). The inductor 1102 receives electrical current from the generator 202 (for instance, from the power source unit 102 thereof) by way of the flexible cord 208 and/or the one or more electrical conductors and/or components that may be interposed between the inductor 1102 and the flexible cord 208.

As described above, the inductor 1102 is inductively coupled to the inductor 1122, the inductor 1122 is connected to the switch 126 within the handle assembly 122, and the handle assembly 122 is stationary relative to the rotatable assembly 130. The stationary assembly 127 includes the handle assembly 122 and the housing unit 123. The inductor 1122 is also stationary relative to the rotatable assembly 130 and the inductor 1122 is stationary relative to the inductor 1102. The inductor 1102 is rotatable relative to the stationary assembly 127. There is no physical connection between the inductor 1102 and the inductor 1122. Therefore, the inductor 1102 and the inductor 1122 are rotatable relative to each other. Thus, the degree of rotation by the rotatable assembly 130 relative to the stationary assembly 127 is not hindered by the inductors 1102, 1122. The inductor 1102 and the inductor 1122 are inductively coupled to one another and form a coupled transformer (for example, a weakly coupled transformer). The inductors 1102, 1122 are thus communicatively coupled to each other and form a contactless connection. Communication of signals, power, and/or other information between the inductors 1102, 1122 is facilitated and maintained at all positions of the rotatable assembly 130. In some embodiments, a current signal propagating in one portion (for instance a primary side) of the coupled transformer formed by the inductors 110, 1122 causes a corresponding current signal to propagate in another portion (for instance a secondary side) of the coupled transformer formed by the inductors 110, 1122.

Figure 3:
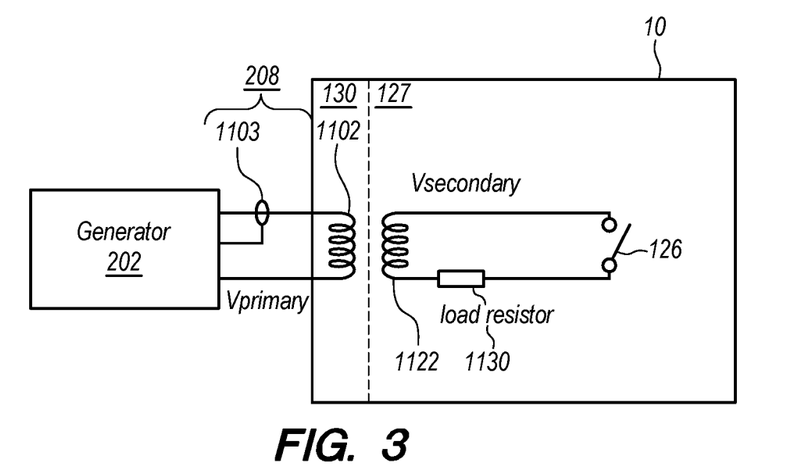
FIG. 3 is a schematic view, which shows one illustrative embodiment of a circuit topology of a portion of the integrated corded surgical system of FIG. 1, in accordance with the present disclosure.

Having described aspects of the example surgical system 1 in the contexts of FIG. 1 and FIG. 2, aspects of example circuit topologies for the switch 126 of the surgical system 1 will be described with reference to FIG. 3 and FIG. 4, in accordance with various example embodiments. Referring initially to FIG. 3, an illustrative embodiment of a circuit topology of a portion of the integrated corded surgical system 1 is shown, where the surgical device 10 includes a single switch 126 that is capable of being set to any one of two positions. The particular switch configuration illustrated in FIG. 3 is provided merely as an example, but other switch configurations are contemplated as well. For instance, the switch 126, in some embodiments, could be capable of being set to one of more than two positions. Further, as described below in the context of FIG. 4, the surgical device 10, in some embodiments, includes multiple switches 126-1, 126-2, and 126-3, each of which is capable of being set to any one of multiple possible positions.

The switch 126 shown in FIG. 3 is a two-position switch 126 that is housed in the stationary assembly 127 and is coupled to the generator 202 (more particularly, in an example, to a sensing circuit 100 thereof, as described below in the context of FIG. 5) by way of the inductor 1122, the inductor 1102, the cord 208, and the current sensor 1103. As described in further detail below, the generator 202 (more particularly, for example, sensing circuitry 100 thereof) drives the inductor 1102 with a constant (or approximately constant) voltage, and the inductors 1102, 1122 are coupled to one another such that one or more attributes of a current signal propagating through the inductor 1102 changes based on the position to which the switch 126 (coupled to the inductor 1122) is set. For instance, the inductors 1102, 1122, in an embodiment, are configured such that a first amount of current propagates through the inductor 1102 when the switch 126 is closed and a second amount of current, different from the first amount of current, propagates through the inductor 1102 when the switch 126 is open. As described in further detail below, the generator 202 is configured to detect one or more attributes of a current signal (for example, a peak magnitude of the current signal, an average magnitude of the current signal, a phase of the current signal, a frequency of the current signal, and/or any other attribute of the current signal) propagating through the inductor 1102 operatively coupled to the generator 202. In some embodiments, the generator 202 is configured to compare the detected attribute of the current signal to a particular threshold current signal attribute value and, based on a result of the comparing, deliver to the surgical device 10 (for example, to the rotatable assembly 130, or more particularly, the inductor 1102, the transducer 110, the piezoelectric discs 160, and/or another portion of the surgical device 10) a corresponding driving signal with corresponding signal characteristics at the corresponding power level. One or more threshold values of current signal attributes for the various operative modes in which the surgical device 10 is configured to operate, and the corresponding driving signal at the corresponding power level that is to be delivered by generator 202, are stored in the one or more memories 602 of the generator 202. In various embodiments herein, the driving signal may be any electrical signal that the generator 202 is configured to deliver, such as a radio frequency energy signal, a radio frequency alternating current signal, a microwave energy signal, an electromagnetic signal, and/or any other suitable type of signal.

The position of the switch 126 may be changed by the clinician by moving the position of the switch 126 from an open position to a closed position and from a closed position to an open position. In one example, the amount of current flowing through the inductor 1122 changes based on whether the switch 126 is open or closed, and, by virtue of the inductor 1102 being coupled to the inductor 1122, the amount of current flowing through the inductor 1102 also changes based on whether the switch 126 is open or closed. In this manner, the generator 202 is configured to sense an amount of current propagating through the inductor 1102 and thereby detect a position of the switch 126. For example, when the switch 126 is in a closed position, the current propagating through the inductor 1102 increases relative to the current propagating through the inductor 1102 when the switch 126 is in an open position and the circuit is an open circuit. For instance, when the switch 126 is open, no current flows through the secondary side of the transformer (including the switch 126 and the inductor 1122), and, assuming that the coupled inductors 1122 and 1102 form an ideal transformer, no current flows through the primary side of the transformer (including the generator 202, the current sensor 1103, and the inductor 1102). When the switch 126 is closed, on the other hand, some amount of current flows through the primary side of the transformer (which includes the switch 126, the inductor 1122, and a load represented by the load resistor 1130), and, based on the amount of current that flows through the primary side of the transformer, and based on the coupling factor of the transformer, the generator 202 senses a corresponding amount of current on the secondary side of the transformer (including the inductor 1102). More generally, power and/or data signals (such as signals indicating a position of the switch 126 and thus an operation mode of the surgical device 10, an activation state of the surgical device 10, and/or the like) are communicated across the boundary between the rotatable assembly 130 and the stationary assembly 127 by way of the inductors 1102, 1122 without inhibiting the free rotation of the rotatable assembly 130 relative to the stationary assembly 127.

Figure 4:
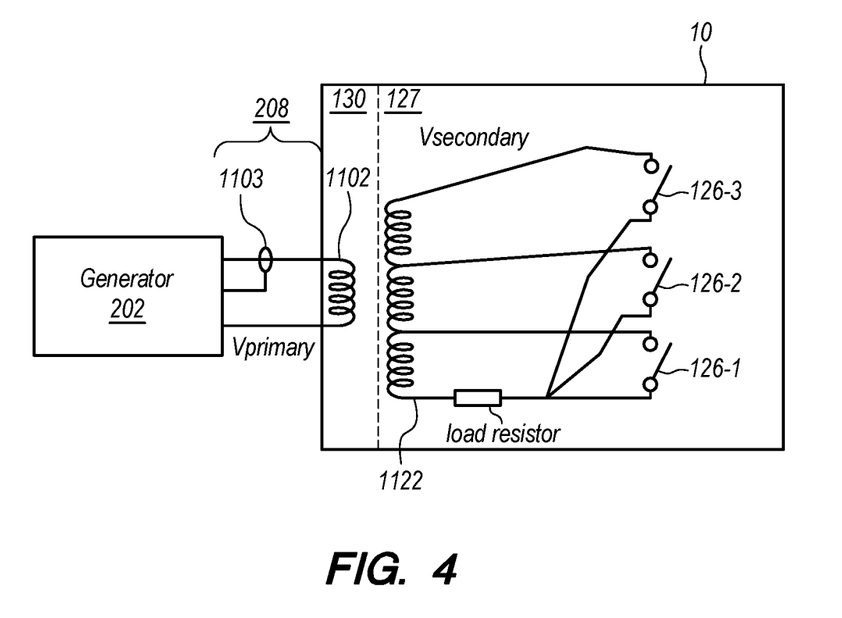
FIG. 4 is a schematic view, which shows another illustrative embodiment of a circuit topology of a portion of the integrated corded surgical system of FIG. 1, in accordance with the present disclosure.

Referring now to FIG. 4, another illustrative embodiment of a circuit topology of a portion of the surgical system 1 is shown, where the surgical device 10 includes multiple switches 126-1, 126-2, and 126-3, each of which is capable of being set to any one of two positions. The particular switch configuration illustrated in FIG. 4 is provided merely as another example, but other switch configurations are contemplated as well. For instance, one or more of the switches 126-1, 126-2, and/or 126-3, in some embodiments, could be capable of being set to one of more than two positions.

The switches 126-1, 126-2, 126-3 are two-position switches that are housed in the stationary assembly 127 and are coupled to the generator 202 (more particularly, in an example, to a sensing circuit 100 thereof, as described below in the context of FIG. 5) by way of the inductor 1122, the inductor 1102, the cord 208, and the current sensor 1103. In one example, each of the switches 126-1, 126-2, 126-3 corresponds to a setting of the surgical device 10 (such as a power enable setting, an operation mode setting, an activation enable setting, and/or another type of setting) and enables a user to alter a state of the setting by altering a position of the corresponding switch. In some embodiments, a user is enabled to set the positions of the switches 126-1, 126-2, 126-3 independently from one another. In other embodiments, only one of the switches 126-1, 126-2, 126-3 may be set to an active position at any given time. For example, the switch 126-3 may be configured to correspond to a high power mode, the switch 126-2 may be configured to correspond to a mid-range power mode, and the switch 126-1 may be configured to correspond to a low power mode of the surgical device 10. Based on which of the switches 126-1, 126-2, and 126-3 are open and which are closed, the amount of current that propagates through the inductor 1122, one or more of the switches 126-1, 126-2, and 126-3, the inductor 1102, and hence the amount of current detected by the current sensor 1103, varies. For example, in an embodiment where the inductor 1102 is driven with a constant (or approximately constant) voltage, the amount of current detected by current sensor 1103 when the switch 126-3 is closed and the switches 126-1 and 126-2 are open is greater than the amount of current detected by the current sensor 1103 when the switch 126-2 is closed and the switches 126-1 and 126-3 are open. Similarly, the amount of current detected by the current sensor 1103 when the switch 126-2 is closed and the switches 126-1 and 126-3 are open is greater than the amount of current detected by the current sensor 1103 when the switch 126-1 is closed and the switches 126-2 and 126-3 are open. In some embodiments, multiple ones of the switches 126-1, 126-2, and 126-3 may be closed (or open) at a time (for instance, the switches 126-1 and 126-2 may be closed while the switch 126-3 is closed), and the current sensor 1103 detects a different amount of current for each of the different possible combinations of positions of the switches 126-1, 126-2, and 126-3.

As described above, the current sensor 1103 transmits information corresponding to the amount of current detected to the generator 202, and, in response, the generator 202 transmits a driving signal of a particular type and/or at a particular power level to the surgical device 10. The particular power level at which the generator 202 transmits the driving signal, in some examples, is based on or corresponds to the current information transmitted to or received by the generator 202. For example, in an embodiment where the inductor 1102 is driven with a constant (or approximately constant) voltage, the amount of current propagating through the inductor 1122 when the switch 126-3 is closed is greater than the amount of current propagating through the inductor 1122 when the switch 126-2 is closed and current information transmitted to or received by the generator 202 when the switch 126-3 is closed reflects the larger current amount detected across the inductor 1122 than when the switch 126-2 is closed. Therefore, the power level at which the generator 202 delivers the driving signal when the switch 126-3 is closed is at a different (for example, a greater) power level than when the switch 126-2 is closed. Thus, selection of the different operative modes and/or configuration of settings of the surgical device 10 are facilitated by way of the switches 126-1, 126-2, and/or 126-3 and corresponding signals are communicated across the boundary between the rotatable assembly 130 and the stationary assembly 127 by way of the inductors 1102, 1122 without inhibiting the free rotation of the rotatable assembly 130 relative to the stationary assembly 127.

In one example embodiment, the generator 202 includes a memory (which is not shown in FIG. 3. or FIG. 4 but, in some examples, is the memory 602 described below in connection with FIG. 6) that stores a table that indicates, for a particular amount of current (for instance, within an amount of variation predetermined to be acceptable) that is detected as propagating through the inductor 1102, and the corresponding position(s) of one or more of the switch 126 (for the embodiment of FIG. 3) or the switches 126-1, 126-2, and 126-3 (for the embodiment of FIG. 4), a corresponding position of the switch 126 (FIG. 3) or the switches 126-1, 126-2, and 126-3 (FIG. 4), and/or a corresponding setting state. The table, for instance, may include multiple entries, with each of the entries associating a particular amount of current with a corresponding configuration of the position(s) of the one or more switches 126 and/or a corresponding setting state. In an embodiment, such as the embodiment of FIG. 3, where the surgical device 10 includes a single switch 126 that has two possible positions (for example, open or closed), the table associates two unique amounts of current with the two possible positions of the switch 126, respectively. In an embodiment, such as the embodiment of FIG. 4, where the surgical device 10 includes multiple switches 126-1, 126-2, and 126-3, each having two possible positions, the table indicates a unique amount of current that is expected to be detected for each possible combination of positions of the switches 126-1, 126-2, and 126-3. Table 1 provided below illustrates an example table for an embodiment where the surgical device includes three switches 126-1, 126-2, and 126-3 each having two possible positions (open or closed).

TABLE 1

| Switch Position | | | | |
|---|---|---|---|---|
| Switch 126-1 | Switch 126-2 | Switch 126-3 | Amount of Current | Setting State |
| Open | Open | Open | Amount 1 | Setting State 1 |
| Open | Open | Closed | Amount 2 | Setting State 2 |
| Open | Closed | Open | Amount 3 | Setting State 3 |
| Open | Closed | Closed | Amount 4 | Setting State 4 |
| Closed | Open | Open | Amount 6 | Setting State 5 |
| Closed | Open | Closed | Amount 7 | Setting State 6 |
| Closed | Closed | Open | Amount 8 | Setting State 7 |
| Closed | Closed | Closed | Amount 9 | Setting State 8 |

The generator 202 determines the respective positions of the one or more switches 126, and hence the setting state, by matching the detected amount of current propagating through the inductor 1102 to the corresponding combination of positions of the switches 126-1, 126-2, and 126-3 indicated in the table. The mapping between setting states and corresponding amounts of current and/or switch positions shown in Table 1 is provided merely as an example. Other mappings are also contemplated. For instance, one particular setting state may correspond to multiple amounts of current.

Figure 5:
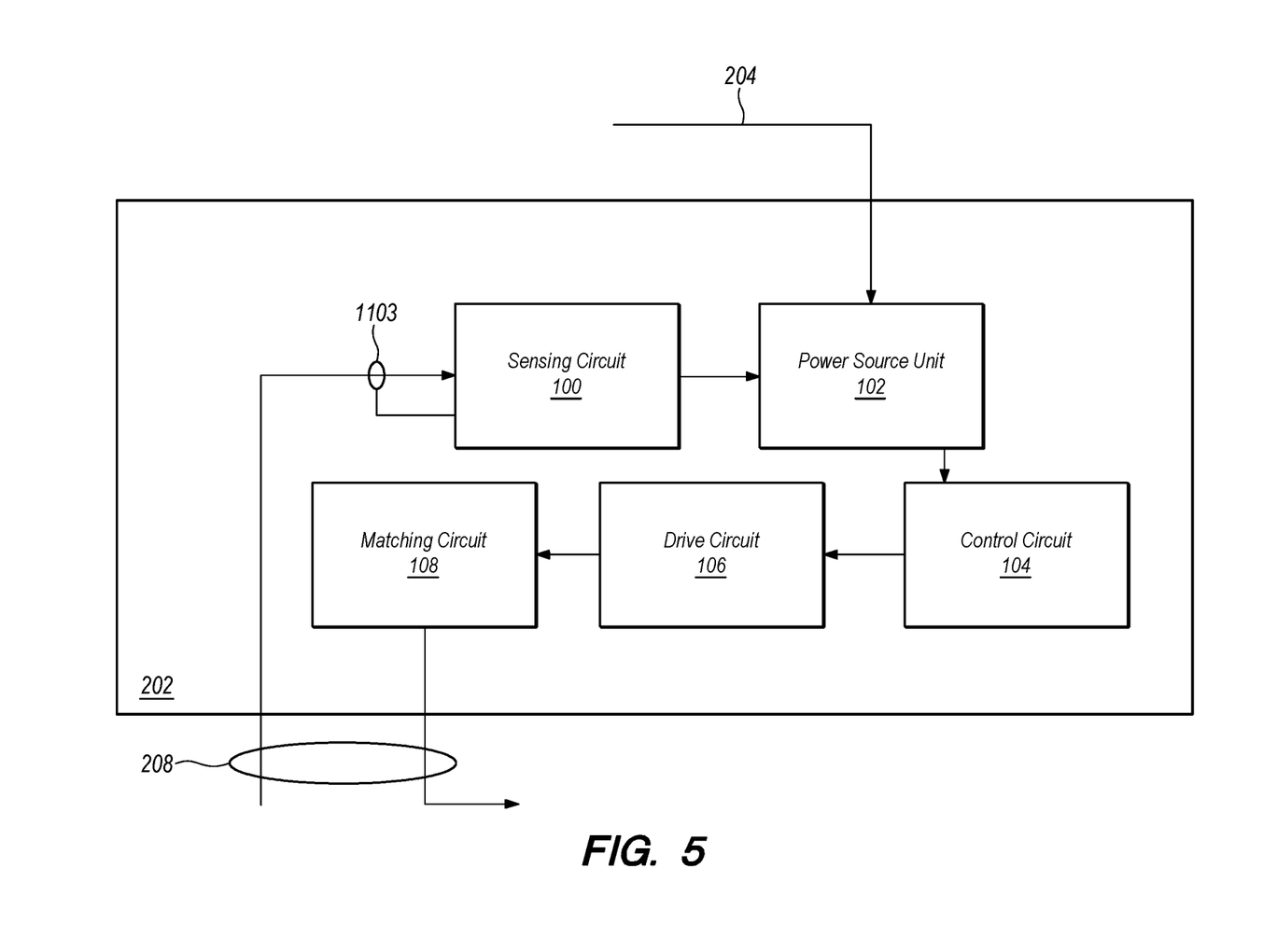
FIG. 5 is a block diagram showing example functional blocks of a generator, in accordance with the present disclosure.

FIG. 5 shows a block schematic diagram of an example of the generator 202 in accordance with various embodiments herein. The generator 202 includes sensing circuitry 100, a current sensor 1103, a power source unit 102, a control circuit 104, a drive circuit 106, and a matching circuit unit 108. In the example configuration shown in FIG. 5, the current sensor 1103 is included in the generator 202 and is coupled to the sensing circuit 100, although other configurations of the current sensor 1103 and/or the sensing circuit 100 are also contemplated. For instance, in various embodiments, the current sensor 1103 and/or the sensing circuit 100 may be disposed in the surgical device 10 or in the flexible cord 208. Further, the sensing circuit 100 may include the current sensor 1103 in some examples.

In general, the power source unit 102 receives electrical power from an electrical outlet 206 by way of the power cord 204 and provides power to other components of the generator 202, such as the sensing circuit 100, the current sensor 1103, the control circuit 104, the drive circuit 106, and/or the matching circuit 108. The drive circuit 106, in some aspects, is configured to utilize the power from the power source unit 102 to generate a high-voltage self-oscillating signal, which is fed to the matching circuit 108. The matching circuit 108 includes signal-smoothing components that, based on the signal received from the drive circuit 106, generate a refined driving signal that is transmitted to the surgical device 10 by way of the cord 208. In some embodiments, the driving signal is transmitted to the transducer 110 within the surgical device 10, thereby causing the mechanical portion of the transducer 110 to move back and forth at a magnitude and frequency that gives rise to a resonance along the waveguide 114.

For optimal resonance and longevity of the resonating instrument and its components, the driving signal applied to the transducer 110 should be as smooth a sine wave as can practically be achieved. For this reason, the matching circuit 108, the transducer 110, and the waveguide 114 are selected to work in conjunction with one another and are all frequency sensitive with and to each other. Resonance is maintained by a phase locked loop (PLL), which creates a closed loop between the output of the matching circuit 108 and the drive circuit 106. Resonance is maintained at varying waveguide 114 load conditions by monitoring and maintaining a constant current applied to the transducer.

As described above, the generator 202 may include one or more processors (not shown in FIG. 5) that are coupled with one or more memory units (not shown in FIG. 5). The generator 202 may be configured with a processing unit (not shown in FIG. 5, but described in further detail below in connection with FIG. 6) capable of executing procedures, such as programs, routines, scripts, or other executable commands necessary for integrating and analyzing data from various components of the generator 202. For instance, in some embodiments, the current sensor 1103 is configured to (1) sense an attribute of a current signal propagating through the inductor 1102 and (2) output to the sensing circuit 100 a signal representative of the sensed attribute of the current signal. The sensing circuit 100 is configured to detect, based on the signal received from the current sensor 1103, changes in the attribute of the current signal propagating through the inductor 1102 that is operatively coupled to the generator 202 by way of the flexible cord 208. In particular, the sensing circuit 100 is configured to determine, based on the detected attribute of the current signal propagating through the inductor 1102, a position to which the switch 126 is set. For example, the sensing circuit 100 may be configured to compare the detected attribute of the current signal to one or more threshold current signal attributes and/or one or more predetermined rules to ascertain the position to which the switch 126 is set. The sensing circuit 100 then forwards information regarding the ascertained position of the switch 126 to the control circuit 104 and/or another component of the generator 202. In this manner, based on the determined position of the switch 126, the control circuit 104 is configured to perform an appropriate action, such as delivering to the surgical device 10 a particular driving signal for a particular operative mode and/or at a particular power level, ceasing the delivery of a driving signal, and/or any other appropriate action.

The generator 202, in some aspects, is configured to receive, by sensing a position to which the switch 126 is set, an instruction to enter an operating mode of the surgical device 10, and determine the type of driving signal to deliver to the surgical device 10 based on the entered operating mode. The generator 202, for instance, may be configured to determine the type of driving signal and/or the power level of a type of driving signal to be provided to the surgical device 10 based on one or more rules that map a particular driving signal or power level of a particular driving signal for a particular operating mode of the surgical device 10. As described herein, a list of rules may include any stored processes, procedures, scripts or programs that are executable by the generator 202. For example, if the operating mode input indicates that the operating mode of the surgical device 10 is a radio frequency operating mode, then the generator 202 may determine, using the one or more lists of rules, that the driving signal for radio frequency operating mode is a radio frequency energy signal and may deliver the radio frequency energy signal as the driving signal to the surgical device 10. Similarly, if the operating mode input indicates that the operating mode of the surgical device 10 is cauterization mode, then the generator 202 may determine the power level of the driving signal to be delivered for cauterization operating mode using the one or more lists of rules.

Figure 6:
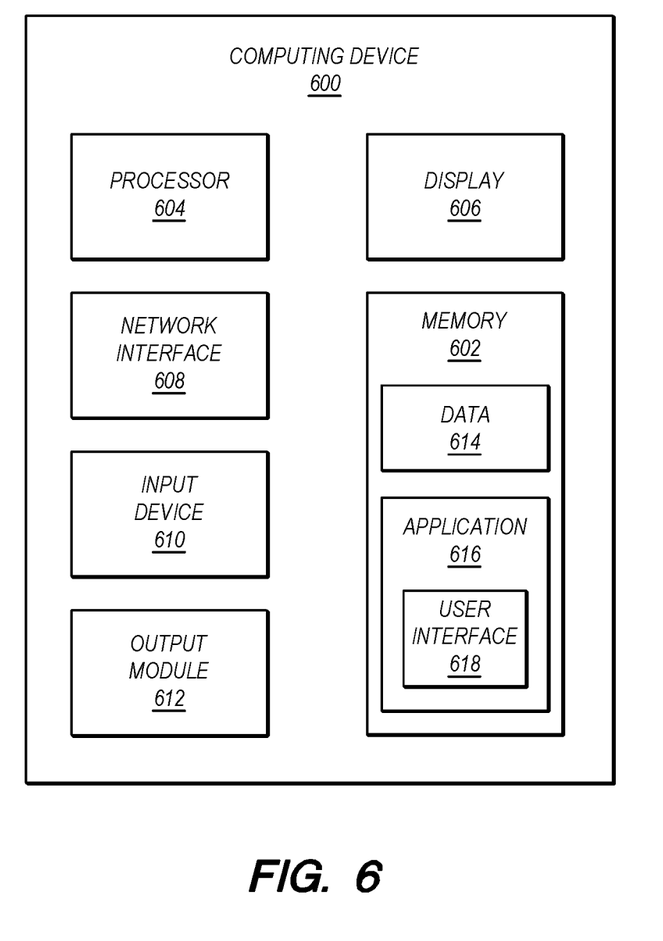
FIG. 6 is a block diagram of an example computing device for use in various embodiments of the present disclosure.

Turning now to FIG. 6, there is shown a block diagram of a computing device 600 that may be employed in accordance with various embodiments herein. For example, one or more components of the computing device 600 may be included within the generator 202, for instance, as implementations of one or more of the sensing circuit 100, the power source unit 102, the control circuit 104, the drive circuit 106, and/or the matching circuit 108, and may be configured to perform one or more steps of one or more procedures and/or algorithms described herein. The computing device 600 may include one or more of a memory 602, a processor 604, a display 606, a network interface 608, an input device 610, and/or an output module 612.

The memory 602 includes any non-transitory computer-readable storage media for storing data and/or software that is executable by the processor 604 and which controls the operation of the computing device 600. In an embodiment, the memory 602 may include one or more solid-state storage devices such as flash memory chips. Alternatively, or in addition to the one or more solid-state storage devices, the memory 602 may include one or more mass storage devices connected to the processor 604 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 604. That is, computer readable storage media include non-transitory, volatile and non-volatile, removable and non-removable media implemented in any method or technology for storage of information such as computer-readable instructions, data structures, program modules or other data. For example, computer-readable storage media include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the computing device 600.

The memory 602 may store application 616 and data 614. The application 616 may, when executed by the processor 604, cause the display 606 to present user interface 618 thereon.

The processor 604 may be a general purpose processor, a specialized graphic processing unit (GPU) configured to perform specific graphics processing tasks while freeing up the general purpose processor to perform other tasks, and/or any number or combination of such processors.

The display 606 may be touch-sensitive and/or voice-activated, enabling the display 606 to serve as both an input and output device. Alternatively, a keyboard (not shown), mouse (not shown), or other data input devices may be employed.

The network interface 608 may be configured to connect to a network such as a local area network (LAN) consisting of a wired network and/or a wireless network, a wide area network (WAN), a wireless mobile network, a Bluetooth network, and/or the internet. The computing device 600 may receive updates to its software, for example, application 616, via network interface 608. The computing device 600 may also display notifications on the display 606 that a software update is available.

The input device 610 may be any device by means of which a user may interact with the computing device 600, such as, for example, a mouse, keyboard, foot pedal, touch screen, and/or voice interface.

The output module 612 may include any connectivity port or bus, such as, for example, parallel ports, serial ports, universal serial busses (USB), or any other similar connectivity port known to those skilled in the art.

The application 616 may be one or more software programs stored in the memory 602 and executed by the processor 604 of the computing device 600. The application 616 may be installed directly on the computing device 600, or may be installed on another computer, for example a central server, and opened on the computing device 600 via the network interface 608. The application 616 may run natively on the computing device 600, as a web-based application, or any other format known to those skilled in the art. In some embodiments, the application 616 will be a single software program having all of the features and functionality described in the present disclosure. In other embodiments, the application 616 may be two or more distinct software programs providing various parts of these features and functionality. In such instances, the various software programs forming part of the application 616 may be enabled to communicate with each other and/or import and export various data including settings and parameters.

The application 616 may communicate with the user interface 618 which generates and presents to a user visual interactive features, for example, on the display 606 and can receive input, for example, via the input device 610. For example, the user interface 618 may generate a graphical user interface (GUI) and output the GUI to the display 606 for viewing by a user.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

The embodiments disclosed herein are examples of the disclosure and may be embodied in various forms. For instance, although certain embodiments herein are described as separate embodiments, each of the embodiments herein may be combined with one or more of the other embodiments herein. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments" may each refer to one or more of the same or different embodiments in accordance with the present disclosure. A phrase in the form "A or B" means "(A), (B), or (A and B)." A phrase in the form "at least one of A, B, or C" means "(A); (B); (C); (A and B); (A and C); (B and C); or (A, B, and C)." The term "clinician" may refer to a clinician or any medical professional, such as a doctor, nurse, technician, medical assistant, or the like, performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, programmable logic device (PLD), field programmable gate array (FPGA), or the like. The controller may also include one or more memories to store data and/or instructions that, when executed by the one or more processors, causes the one or more processors to individually and/or collectively perform one or more steps of one or more methods and/or algorithms.

Any of the herein described methods, programs, algorithms or codes may be converted to, or expressed in, a programming language or computer program. The terms "programming language" and "computer program," as used herein, each include any language used to specify instructions to a computer, and include (but is not limited to) the following languages and their derivatives: Assembler, Basic, Batch files, BCPL, C, C+, C++, Delphi, Fortran, Java, JavaScript, machine code, operating system command languages, Pascal, Perl, PL1, scripting languages, Visual Basic, metalanguages which themselves specify programs, and all first, second, third, fourth, fifth, or further generation computer languages. Also included are database and other data schemas, and any other meta-languages. No distinction is made between languages which are interpreted, compiled, or use both compiled and interpreted approaches. No distinction is made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods, and techniques that are insubstantially different from those described above and/or in the appended claims are also intended to be within the scope of the disclosure. It will be apparent to those of ordinary skill in the art that various modifications to the foregoing embodiments may be made without departing from the scope of the disclosure. For example, various steps of the methods described herein may be implemented concurrently and/or in an order different from the example order(s) described herein.

What is claimed is:
1. A surgical device, comprising:
   a stationary handle;
   a rotatable assembly coupled to the stationary handle, wherein the rotatable assembly is rotatable with respect to the stationary handle;

a plurality of switches coupled to the stationary handle, wherein each switch of the plurality of switches is configured to move, independently from the other switches, between a plurality of positions;
a first inductor coupled to the plurality of switches, the first inductor disposed within the stationary handle separate from the rotatable assembly; and
a second inductor disposed within the rotatable assembly separate from the stationary handle, wherein an amount of current that propagates through the first and second inductors is based on a combination of positions of the plurality of switches.

2. The surgical device of claim 1, wherein the first inductor and the second inductor form a coupling transformer.

3. The surgical device of claim 1, wherein at least one of the first inductor or the second inductor is a contactless ring.

4. The surgical device of claim 1, wherein the first inductor and the second inductor are communicatively coupled to one another, and the first inductor and the second inductor are configured so as to remain communicatively coupled to one another at all positions of the rotatable assembly with respect to the stationary handle.

5. The surgical device of claim 1, wherein the first inductor is disposed out of physical contact with the rotatable assembly.

6. The surgical device of claim 1, wherein the rotatable assembly comprises an end effector.

7. The surgical device of claim 1, wherein the surgical device is an ultrasonic surgical device.

8. The surgical device of claim 1, wherein the surgical device is a radio frequency energy-based surgical device.

9. A surgical system, comprising:
a surgical device, comprising:
 a stationary handle;
 a rotatable assembly coupled to the stationary handle, wherein the rotatable assembly is rotatable with respect to the stationary handle;
 a plurality of switches coupled to the stationary handle, wherein each switch of the plurality of switches is configured to move, independently from the other switches, between a plurality of positions;
 a first inductor coupled to the plurality of switches, the first inductor disposed within the stationary handle separate from the rotatable assembly; and
 a second inductor disposed within the rotatable assembly separate from the stationary handle, wherein an amount of current that propagates through the first and second inductors is based on a combination of positions of the plurality of switches;
a generator; and
a flexible electrical power cord, wherein the rotatable assembly is configured to be coupled to the generator by way of the flexible electrical power cord.

10. The surgical system of claim 9, wherein the first inductor and the second inductor form a coupling transformer.

11. The surgical system of claim 9, wherein the first inductor and the second inductor are communicatively coupled to one another, and the first inductor and the second inductor are configured so as to remain communicatively coupled to one another at all positions of the rotatable assembly with respect to the stationary handle.

12. The surgical system of claim 9, wherein the generator comprises:
an electrical current sensor.

13. The surgical system of claim 12, wherein the electrical current sensor is configured to be coupled to the second inductor by way of the flexible electrical power cord and detect the amount of current propagating through the second inductor.

14. The surgical system of claim 13, wherein the generator is configured to deliver a driving signal to the rotatable assembly, via the flexible electrical power cord, in response to the electrical current sensor detecting a threshold amount of current across the second inductor.

15. The surgical system of claim 9, wherein the generator further comprises:
a processor;
a memory unit coupled to the processor; and
sequences of instructions stored in the memory unit which, when executed, cause the processor to:
 deliver a driving signal to the rotatable assembly.

16. The surgical system of claim 15, wherein the memory further stores sequences of instructions which, when executed, cause the processor to:
receive information relating to an operating mode of the surgical device; and
deliver, based on the information relating to the operating mode of the surgical device, a particular driving signal to the rotatable assembly.

17. The surgical system of claim 16, wherein the operating mode of the surgical device is a radio frequency mode and wherein the particular driving signal delivered to the rotatable assembly is a radio frequency signal.

18. The surgical system of claim 16, wherein the operating mode of the surgical device is a cauterization mode and the memory further stores sequences of instructions which, when executed, cause the processor to:
deliver, as the driving signal, a signal corresponding to the cauterization mode.

19. The surgical system of claim 16, wherein the operating mode of the surgical device is a coagulation mode and the memory further stores sequences of instructions which, when executed, cause the processor to:
deliver, as the driving signal, a signal corresponding to the coagulation mode.

* * * * *